US012637667B2

(12) United States Patent
Yagi et al.

(10) Patent No.: US 12,637,667 B2
(45) Date of Patent: May 26, 2026

(54) FokI NUCLEASE DOMAIN MUTANT

(71) Applicants: EDITFORCE INC., Fukuoka (JP); Kyushu University, National University Corporation, Fukuoka (JP)

(72) Inventors: Yusuke Yagi, Fukuoka (JP); Masaru Ohta, Fukuoka (JP); Takahiro Nakamura, Fukuoka (JP)

(73) Assignees: EditForce, Inc., Fukuoka (JP); Kyushu University, National University Corporation, Fukuoka (JP)

( * ) Notice: Subject to any disclaimer, the term of this patent is extended or adjusted under 35 U.S.C. 154(b) by 466 days.

(21) Appl. No.: 18/035,430

(22) PCT Filed: Nov. 4, 2021

(86) PCT No.: PCT/JP2021/040503
§ 371 (c)(1),
(2) Date: May 4, 2023

(87) PCT Pub. No.: WO2022/097663
PCT Pub. Date: May 12, 2022

(65) Prior Publication Data
US 2023/0416709 A1      Dec. 28, 2023

(30) Foreign Application Priority Data
Nov. 6, 2020      (JP) ................................. 2020-185619

(51) Int. Cl.
*C12N 9/22*      (2006.01)
*C12N 15/62*      (2006.01)
*C12N 15/63*      (2006.01)

(52) U.S. Cl.
CPC .............. *C12N 9/22* (2013.01); *C12N 15/62* (2013.01); *C12N 15/63* (2013.01); *C12N 2310/20* (2017.05)

(58) Field of Classification Search
CPC ......... C12N 9/22; C12N 15/62; C12N 15/63; C12N 2310/20
See application file for complete search history.

(56) References Cited

U.S. PATENT DOCUMENTS

2013/0217131 A1      8/2013   Kim et al.
2019/0153061 A1      5/2019   Brogdon et al.

FOREIGN PATENT DOCUMENTS

WO      2011/091324 A2      7/2011
WO      2011/097036 A1      8/2011
WO      2018/039448 A1      3/2018

OTHER PUBLICATIONS

Miller et al., Enhancing gene editing specificity by attenuating DNA cleavage kinetics. Nat Biotechnol. Aug. 2019;37(8):945-952. doi: 10.1038/s41587-019-0186-z. Epub Jul. 29, 2019. PMID: 31359006. (Year: 2019).*
International Preliminary Report on Patentability dated May 8, 2023, with English translation of Written Opinion, issued in International Application No. PCT/JP2021/040503.
Jurate Bitinaite, et al., "FokI dimerization is required for DNA cleavage", Proc. Natl. Acad. Sci., Sep. 1998, pp. 10570-10575, vol. 95.
David S. Waugh, et al., "A Novel Class of Fok1 Restriction Endonuclease Mutants That Cleave Hemi-methylated Substrates", The Journal of Biological Chemistry, Issue of Apr. 22, 1994, pp. 12298-12303, vol. 269, No. 16.
Jeffrey C. Miller, et al., "Enhancing gene editing specificity by attenuating DNA cleavage kinetics", Nature Biotechnology, Aug. 2019, pp. 945-952, vol. 37.
Jing Guo, et al., "Directed Evolution of an Enhanced and Highly Efficient FokI Cleavage Domain for Zinc Finger Nucleases", J. Mol. Biol., 2010, pp. 96-107, vol. 400.
International Search Report for PCT/JP2021/040503 dated Nov. 30, 2021 [PCT/ISA/210].
Benjamin et al., "TALEN gene editing takes aim on HIV", Human Genetics, 2016, 12 pages.
Partial Supplementary European Search Report dated Aug. 20, 2024 in application No. 21889216.4.

* cited by examiner

*Primary Examiner* — Louise W Humphrey
*Assistant Examiner* — Rachel Emily Martin
(74) *Attorney, Agent, or Firm* — Sughrue Mion, PLLC

(57)      ABSTRACT

It was found that four nuclease domain mutants have nuclease activity superior to that of a wild-type nuclease domain and are capable of enhancing genome editing efficiency in combination with various nucleic acid binding domains.

8 Claims, 5 Drawing Sheets
Specification includes a Sequence Listing.

Fig. 1

M47 MUTANT
(SEQ ID NO: 11)

QLMKSELEEKKSELRRKLKYVPHEYIELIEIARNSTQYRIFEMKVMEFLVKVYGYRGKHLGGSRNP
DGAIYTVGSPIDYGVIIDTKAYSGGYNLPIGQADAMLRYVEENQTRNKHINPNEWWKVYPSSVTEF
KFLFVSGHFKGNYKAQLTRLNHITNCNGAVLSVEELLIGGEMIKAGTLTLEEVRRKFNNGEINF*

M48 MUTANT
(SEQ ID NO: 12)

QLVKSELEEKKSELRHKLKYVPHEYIELIEIARNPTLDRILEMKVMEFFMKVYGYRGKHLGGSRKP
DGVIYTVGSPIDYGVIVDTKAYSRGYNLPIGQADEMHRYVVENQTRNKLINPNEWWKVYPSSVTEF
KFLFVSGHFKGNYKAQLTRLNHITNCKGAVLSVEELLIGGEMIRAGTLTLEEVRSKFNNGEINF*

M49 MUTANT
(SEQ ID NO: 13)

QLMKSELEEKKEELRRKLKYVPHEYIELIEIARNSTQYRIFEMKVMEFLVKVYGYRGKHLGGSRNP
DGAIYTVGSPIDYGVIVDTKAYSGGYNLPIGQADAMLRYVEENQTRNKHINPNEWWKVYPSSVTEF
KFLFVSGHFKGNYKAQLTRLNHITNCNGAVLSVEELLIGGEMIKAGTLTLEEVRRKFNNGEINF*

M50 MUTANT
(SEQ ID NO: 14)

QPVKSELEEKKAELRHKLKYVPHEYIELIEIARNSTQDRILEMMVMEFFMKVYGYRGKHLGGSRKP
DGVIYTVGSPFDYGVIVDTKAYSRGYNLPIGHADEMQRYVQBNQTRNKHINPNEWWKVYPSSVTEF
KFLFVSGHFKGNYKAQLTRLNHITNCTGAVLSVEELLIGGEMIRAGTLTLEEVRSKFNNGEINF*

FokI NUCLEASE DOMAIN MUTANT

CROSS REFERENCE TO RELATED APPLICATIONS

This application is a National Stage of International Application No. PCT/JP2021/040503 filed Nov. 4, 2021, claiming priority based on Japanese Patent Application No. 2020-185619 filed Nov. 6, 2020.

INCORPORATION BY REFERENCE OF SEQUENCE LISTING

The content of the electronically submitted sequence listing, file name: Q285469_SEQ_LIS_AS_FILED.txt; size: 17,303 bytes; and date of creation: May 2, 2023, filed herewith, is incorporated herein by reference in its entirety.

TECHNICAL FIELD

The present invention relates to FokI nuclease domain mutants, artificial nucleic acid cleaving enzymes containing the mutants, and uses of them.

BACKGROUND ART

Genome editing is required to introduce a DNA deletion, insertion, base substitution, or the like into a target site in a gene to be modified with high probability. Molecules for use in genome editing (genome editing tool) are composed of a nucleic acid binding domain that binds to a target sequence on the genome and a catalytic domain that cleaves double-stranded DNA near the target sequence. In a case of constructing genome editing tools using DNA binding proteins such as zinc finger proteins (ZFNs), transcription activator-like effector (TALE) proteins, and pentatricopeptide repeat (PPR) proteins, it is general to use a catalytic domain (FokI-CD) of FokI, a Type IIS restriction endonuclease, which has the activity of cleaving double-stranded DNA. In order for FokI to cleave double-stranded DNA, FokI has to dimerize two molecules of FokI-CD (NPL 1). For this reason, a genome editing tool constructed by fusing FokI-CD also uses two molecules whose target sequences are a sense strand and an antisense strand around a target site to be modified.

Regarding a genome editing tool constructed by fusing FokI-CD, such as zinc finger nucleases, the editing efficiency of the genome editing tool has been improved by modifying FokI-CD. For example, an improved FokI-CD (Sharkey variant) with genome editing efficiency improved by introducing random mutations into ZFNs and using an artificial evolution system of *Escherichia coli* has been isolated (NPL 2). However, TALEN fused with FokI-CD containing the Sharkey variant demonstrated no difference in editing efficiency from the wild-type.

CITATION LIST

Non Patent Literature

[NPL 1] Bitinaite J, et al., (1998) Proc Natl Acad Sci USA. 95: 10570-10575.
[NPL 2] Guo J, et al., (2010) J Mol Biol. 400: 96-107.

SUMMARY OF INVENTION

Technical Problem

As a result of further performance evaluation of FokI-CD having the Sharkey variant described in NPL 2 above, the present inventors found that, even when fused with PPR proteins as nucleic acid binding domains, the FokI-CD demonstrated no improvement in the genome editing efficiency as compared to the wild-type. Therefore, there is a problem that FokI-CD having the Sharkey variant is not usable in combination with a wide range of nucleic acid binding domains in genome editing systems.

The present invention has been made in view of such circumstances, and has an object to provide a nuclease domain mutant usable in combination with various nucleic acid binding domains in genome editing and capable of improving genome editing efficiency.

Solution to Problem

As a result of screenings of highly active nuclease domain mutants using an artificial evolution system of *Escherichia coli* to achieve the above object, the present inventors have found that four nuclease domain mutants bound to TALE have superior nuclease activity to that of the wild-type nuclease domain, and that the use of these nuclease domain mutants leads to improved genome editing efficiency. Among these nuclease domain mutants, two nuclease domain mutants retain a common mutation at 473 position, and this common mutation significantly contributed to the improvement of the nuclease activity. In addition, even when fused with PPRs, these nuclease domain mutants demonstrated an improvement in genome editing efficiency. Based on the above, the present inventors have found that the constructed nuclease domain mutants have excellent nuclease activity and are usable for genome editing in combination with various nucleic acid binding domains, and have completed the present invention.

The present invention relates to highly active nuclease domain mutants, artificial nucleic acid cleaving enzymes comprising the nuclease domain mutants, and uses of them, and more specifically provides the followings.

[1] A nuclease domain mutant of a FokI protein or a homologous protein thereof, which has a mutation listed in any of (a) to (d) below, and whose nuclease activity is improved by the mutation:

(a) at least one mutation selected from the group consisting of a substitution of amino acid with Met at position 386 in the FokI protein or the corresponding site in the homologous protein, a substitution of amino acid with Arg at position 399 in the FokI protein or the corresponding site in the homologous protein, a substitution of amino acid with Tyr at position 421 in the FokI protein or the corresponding site in the homologous protein, a substitution of amino acid with Phe at position 424 in the FokI protein or the corresponding site in the homologous protein, a substitution of amino acid with Leu at position 432 in the FokI protein or the corresponding site in the homologous protein, a substitution of amino acid with Val at position 433 in the FokI protein or the corresponding site in the homologous protein, a substitution of amino acid with Asn at position 448 in the FokI protein or the corresponding site in the homologous protein, a substitution of amino acid with Ile at position 466 in the FokI protein or the corresponding site in the homologous protein, a substitution of amino acid with Ala at position 484 in the FokI protein or the corresponding site in the homologous protein, and a substitution of amino acid with Leu at position 486 in the FokI protein or the corresponding site in the homologous protein;

(b) at least one mutation selected from the group consisting of a substitution of amino acid with Pro at position 418 of a wild-type protein or the corresponding site of a homologous protein thereof, a substitution of amino acid with Leu at position 420 in the FokI protein or the corresponding site in the homologous protein, a substitution of amino acid with Val at position 452 in the FokI protein or the corresponding site in the homologous protein, a substitution of amino acid with Arg at position 473 in the FokI protein or the corresponding site in the homologous protein, a substitution of amino acid with His at position 486 in the FokI protein or the corresponding site in the homologous protein, a substitution of amino acid with Val at position 490 in the FokI protein or the corresponding site in the homologous protein, a substitution of amino acid with Leu at position 498 in the FokI protein or the corresponding site in the homologous protein, a substitution of amino acid with Lys at position 542 in the FokI protein or the corresponding site in the homologous protein, a substitution of amino acid with Arg at position 559 in the FokI protein or the corresponding site in the homologous protein, and a substitution of amino acid with Ser at position 570 in the FokI protein or the corresponding site in the homologous protein;

(c) at least one mutation selected from the group consisting of a substitution of amino acid with Met at position 386 of a wild-type protein or the corresponding site of a homologous protein thereof, a substitution of amino acid with Phe at position 395 in the FokI protein or the corresponding site in the homologous protein, a substitution of amino acid with Arg at position 399 in the FokI protein or the corresponding site in the homologous protein, a substitution of amino acid with Tyr at position 421 in the FokI protein or the corresponding site in the homologous protein, a substitution of amino acid with Phe at position 424 in the FokI protein or the corresponding site in the homologous protein, a substitution of amino acid with Leu at position 432 in the FokI protein or the corresponding site in the homologous protein, a substitution of amino acid with Val at position 433 in the FokI protein or the corresponding site in the homologous protein, a substitution of amino acid with Asn at position 448 in the FokI protein or the corresponding site in the homologous protein, a substitution of amino acid with Ala at position 484 in the FokI protein or the corresponding site in the homologous protein, and a substitution of amino acid with Leu at position 486 in the FokI protein or the corresponding site in the homologous protein; and (d) at least one mutation selected from the group consisting of a substitution of amino acid with Pro at position 385 of a wild-type protein or the corresponding site of a homologous protein thereof, a substitution of amino acid with Ala at position 395 in the FokI protein or the corresponding site in the homologous protein, a substitution of amino acid with Met at position 427 in the FokI protein or the corresponding site in the homologous protein, a substitution of amino acid with Val at position 452 in the FokI protein or the corresponding site in the homologous protein, a substitution of amino acid with Phe at position 460 in the FokI protein or the corresponding site in the homologous protein, a substitution of amino acid with Arg at position 473 in the FokI protein or the corresponding site in the homologous protein, a substitution of amino acid with His at position 481 in the FokI protein or the corresponding site in the homologous protein, a substitution of amino acid with Gln at position 490 in the FokI protein or the corresponding site in the homologous protein, a substitution of amino acid with Thr at position 542 in the FokI protein or the corresponding site in the homologous protein, a substitution of amino acid with Arg at position 559 in the FokI protein or the corresponding site in the homologous protein, a substitution of amino acid with Ser at position 570 in the FokI protein or the corresponding site in the homologous protein.

[2] The mutant according to [1], which is a nuclease domain mutant of a FokI protein or a homologous protein thereof, which has a mutation in which amino acid is substituted with Arg at position 473 in the FokI protein or the corresponding site in the homologous protein, and whose nuclease activity is improved by the mutation.

[3] An artificial nucleic acid cleaving enzyme comprising a nucleic acid binding domain and the nuclease domain mutant according to [1] or [2]. [4] The artificial nucleic acid cleaving enzyme according to [3], wherein the nucleic acid binding domain is TALE, zinc finger, PPR, or CRISPR-Cas.

[5] A polynucleotide encoding the nuclease domain mutant according to [1] or [2] or the artificial nucleic acid cleaving enzyme according to [3] or [4].

[6] A vector comprising the polynucleotide according to [5].

[7] A cell to which the polynucleotide according to [5] or the vector according to [6] is introduced.

[8] A method for producing a genome-edited cell or non-human organism, comprising introducing, to the cell or the non-human organism, the artificial nucleic acid cleaving enzyme according to [3], a polynucleotide encoding the artificial nucleic acid cleaving enzyme, or a vector containing the polynucleotide.

[9] A kit for genome editing of a cell or organism, comprising the artificial nucleic acid cleaving enzyme according to [3], a polynucleotide encoding the artificial nucleic acid cleaving enzyme, or a vector containing the polynucleotide.

Advantageous Effects of Invention

The nuclease domain mutants according to the present invention are capable of exhibiting superior nuclease activity to that of wild-type nuclease domains. Use of artificial nucleic acid cleaving enzymes constructed by fusing the nuclease domains of the present invention with nucleic acid binding domains such as TALE or PPR enables efficient genome editing.

BRIEF DESCRIPTION OF DRAWINGS

FIG. 1 is a diagram presenting amino acid sequences of four types of FokI nuclease domain mutants. The amino acid sequences at positions 384 to 579 corresponding to the FokI nuclease domains are presented. Underlined positions indicate mutation sites that differ from wild-type FokI.

DESCRIPTION OF EMBODIMENTS

<Nuclease Domain Mutant>

Figure 2:
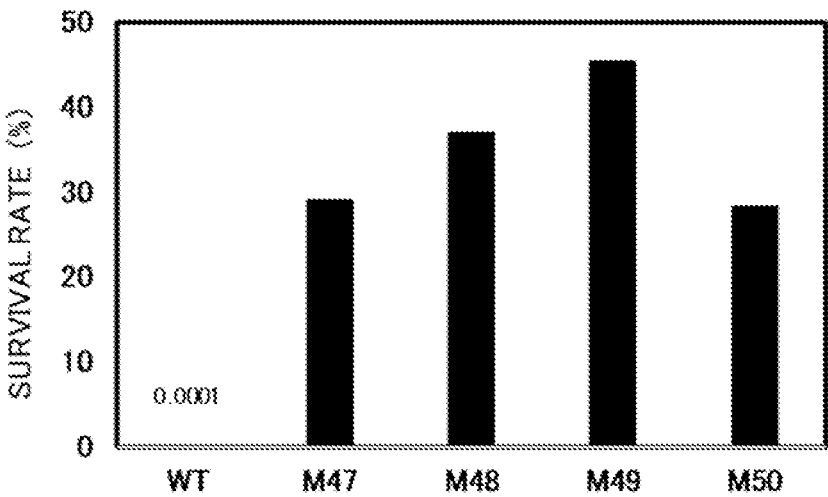
FIG. 2 is a diagram presenting results of evaluating the nuclease activity of the FokI nuclease domain mutant types using, as an index, a survival rate in an artificial evolution system (B2P) of *Escherichia coli*. The survival rate is a value obtained by dividing the number of colonies on an arabinose-supplemented plate by the number of colonies on a non-arabinose-supplemented plate. WT is a wild-type FokI nuclease domain fused with a TALEN-A effector, and the numeric value in the diagram is a survival rate in the case of using the wild-type FokI nuclease domain.

The present invention provides nuclease domain mutants of a FokI protein or a homologous protein thereof.

The "FokI protein" in the present invention is a type IIS restriction endonuclease found in *Flavobacterium okeanokoites* in nature. The FokI protein has activity to catalyze cleavage of double-stranded DNA, at a position 9 nucleotides away from the recognition site in one strand and at a position 13 nucleotides away from the recognition site in the other strand. The FokI protein has a nucleic acid binding domain on the N-terminal side and a nuclease domain (DNA cleavage domain) on the C-terminal side.

The amino acid sequence of a typical wild-type FokI protein is presented in SEQ ID NO: 1 and the amino acid sequence of its nuclease domain is presented in SEQ ID NO: 2. In SEQ ID NO: 1, positions 384 to 579 correspond to the nuclease domain. The nuclease domain mutant of the present invention is obtained by introducing a specific mutation into the nuclease domain of the FokI protein, and has the nuclease activity improved compared to the wild-type nuclease domain.

An embodiment of the FokI nuclease domain mutant of the present invention is a nuclease domain mutant having any of mutations introduced into M47 of Example to be described later, and specifically having at least one mutation selected from the group consisting of a substitution of amino acid with Met at position 386 in the FokI protein, a substitution of amino acid with Arg at position 399 in the FokI protein, a substitution of amino acid with Tyr at position 421 in the FokI protein, a substitution of amino acid with Phe at position 424 in the FokI protein, a substitution of amino acid with Leu at position 432 in the FokI protein, a substitution of amino acid with Val at position 433 in the FokI protein, a substitution of amino acid with Asn at position 448 in the FokI protein, a substitution of amino acid with Ile at position 466 in the FokI protein, a substitution of amino acid with Ala at position 484 in the FokI protein, and a substitution of amino acid with Leu at position 486 in the FokI protein.

Another embodiment of the FokI nuclease domain mutant of the present invention is a nuclease domain mutant having any of mutations introduced into M48 of Example to be described later, and specifically having at least one mutation selected from the group consisting of a substitution of amino acid with Pro at position 418 in a wild-type protein, a substitution of amino acid with Leu at position 420 in the FokI protein, a substitution of amino acid with Val at position 452 in the FokI protein, a substitution of amino acid with Arg at position 473 in the FokI protein, a substitution of amino acid with His at position 486 in the FokI protein, a substitution of amino acid with Val at position 490 in the FokI protein, a substitution of amino acid with Leu at position 498 in the FokI protein, a substitution of amino acid with Lys at position 542 in the FokI protein, a substitution of amino acid with Arg at position 559 in the FokI protein, and a substitution of amino acid with Ser at position 570 in the FokI protein.

Another embodiment of the FokI nuclease domain mutant of the present invention is a nuclease domain mutant having any of mutations introduced into M49 of Example to be described later, and specifically having at least one mutation selected from the group consisting of a substitution of amino acid with Met at position 386 in a wild-type protein, a substitution of amino acid with Phe at position 395 in the FokI protein, a substitution of amino acid with Arg at position 399 in the FokI protein, a substitution of amino acid with Try at position 421 in the FokI protein, a substitution of amino acid with Phe at position 424 in the FokI protein, a substitution of amino acid with Leu at position 432 in the FokI protein, a substitution of amino acid with Val at position 433 in the FokI protein, a substitution of amino acid with Asn at position 448 in the FokI protein, a substitution of amino acid with Ala at position 484 in the FokI protein, and a substitution of amino acid with Leu at position 486 in the FokI protein.

Another embodiment of the FokI nuclease domain mutant of the present invention is a nuclease domain mutant having any of mutations introduced into M50 of Example to be described later, and specifically having at least one mutation selected from the group consisting of a substitution of amino acid with Pro at position 385 in a wild-type protein, a substitution of amino acid with Ala at position 395 in the FokI protein, a substitution of amino acid with Met at position 427 in the FokI protein, a substitution of amino acid with Val at position 452 in the FokI protein, a substitution of amino acid with Phe at position 460 in the FokI protein, a substitution of amino acid with Arg at position 473 in the FokI protein, a substitution of amino acid with His at position 481 in the FokI protein, a substitution of amino acid with Gln at position 490 in the FokI protein, a substitution of amino acid with Thr at position 542 in the FokI protein, a substitution of amino acid with Arg at position 559 in the FokI protein, and a substitution of amino acid with Ser at position 570 in the FokI protein.

An example of the preferred mutations in the FokI nuclease domain mutants of the present invention is a substitution of amino acid with Arg at position 473 in the FokI protein.

Each of the mutants may have a combination of two or more mutations, a combination of three or more mutations, a combination of four or more mutations, or a combination of five or more (for example, six or more, seven or more, eight or more, nine or more, and ten or more) mutations.

Alternatively, the nuclease domain mutants of the present invention may be nuclease domain mutants of homologous proteins of a native FokI protein (hereinafter referred to as "homologous protein nuclease domain mutants"). The "homologous protein" mentioned herein means a protein whose amino acid sequence homology determined by comparing the nuclease domain thereof with the nuclease domain of the native FokI protein is at least 70% or more, preferably 80% or more, and more preferably 90% or more (for example, 95% or more, 96% or more, 97% or more, 98% or more, or 99% or more). In the homologous protein nuclease domain mutant, the amino acid at a site corresponding to the mutation site in the FokI nuclease domain mutant described above is substituted with the same amino acid as in the mutation site in the FokI nuclease domain mutant. The homologous protein may be derived from an organism other than *Flavobacterium okeanokoites*.

The "amino acid sequence homology" can be determined by using sequence analysis software (for example BLAST; blast.ncbi.nlm.nih.gov/Blast.cgi). Then, by using the above amino acid sequence analysis software (for example, BLAST; blast.ncbi.nlm.nih.gov/Blast.cgi), an amino acid at a "site corresponding to" a specific amino acid in the FokI protein can be determined to be an amino acid at the same position as the mutation site when the amino acid sequence of the homologous protein is aligned with the amino acid sequence of the FokI protein. The amino acid sequence analysis by software may use, for example, default parameter setting.

A preferred embodiment of the nuclease domain mutants of the present invention is a mutant having a substitution of amino acid with Arg at position 473 in the FokI protein or the corresponding site of the homologous protein thereof.

Moreover, the nuclease domain mutant (FokI nuclease domain mutant or homologous protein nuclease domain mutant) of the present invention may have one or plural amino acid mutations other than the above mutation site (substitution, deletion, addition, and/or insertion) introduced thereto. The "plural" mentioned herein is not particularly limited but may mean usually 2 to 50, preferably 2 to 30, more preferably 2 to 20, and further preferably 2 to 10 (for example, 2 to 8, 2 to 4, or 2). An example of the useful mutations is a heterodimerization mutation (Doyon Y, et al., (2011) Nat Methods 8: 74-79), for example.

As a method for site-directed mutagenesis, it is possible to use known methods such, for example, as a Kunkel method (Kunkel, T. A. Proc Natl Acad Sci USA (1985), 82 (2): 488-492), an ODA method (Hashimoto-Gotoh et al., (1995) Gene 152: 271-276), and a SOE (splicing-by-overlap-extention)-PCR method (Ho, S. N. et al., (1989) Gene 77: 51-59). Commercially available site-directed mutagenesis kits may be used.

Figure 4:
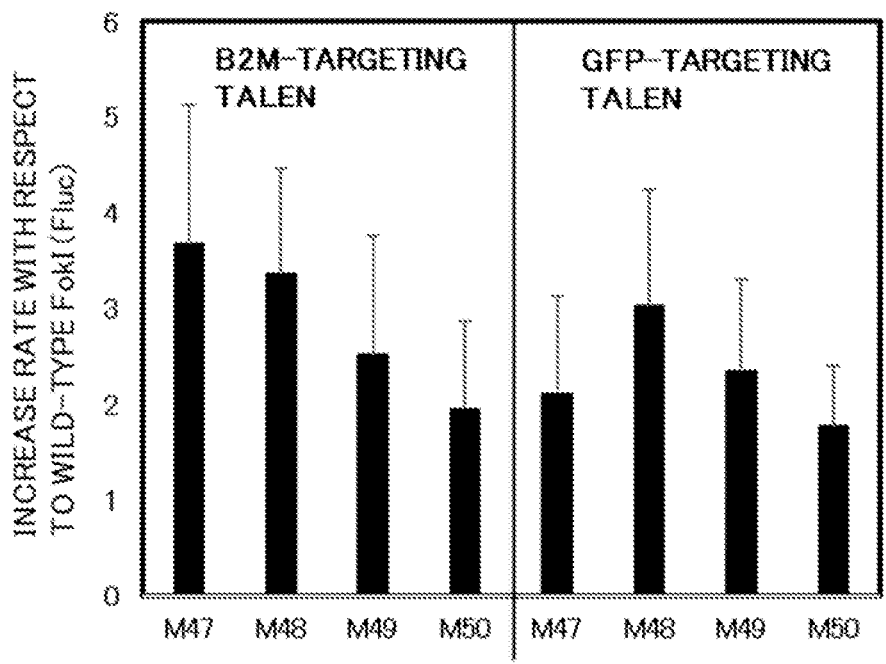
FIG. 4 is a diagram presenting results of a target reporter assay using TALENs targeting a B2M gene or a GFP gene. The graph indicates an increase rate (fold) in the activity of each of the FokI nuclease domain mutants with respect to the wild-type FokI nuclease domain. The values are an average value and a standard error of three independent experiments.
Figure 5:
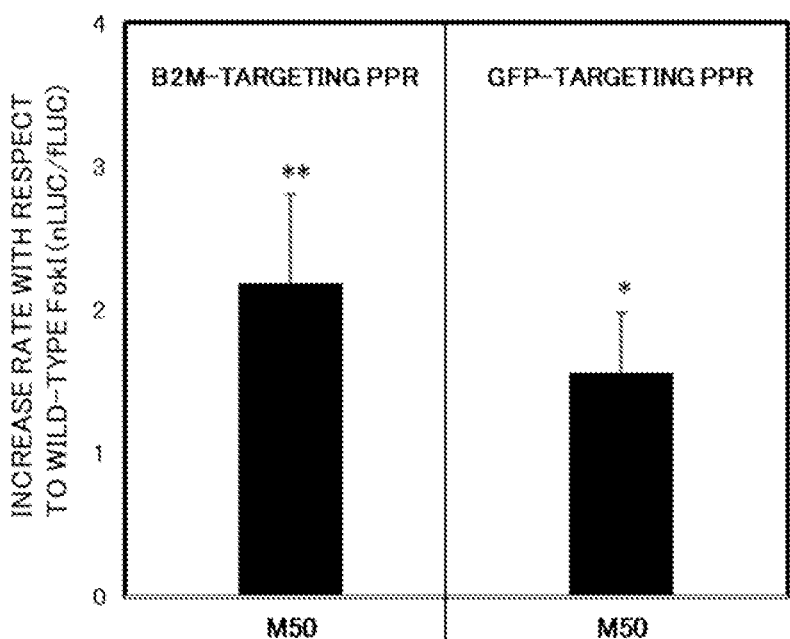
FIG. 5 is a diagram presenting results of a target reporter assay using PPRs targeting the B2M gene or the GFP gene. The graph indicates an increase rate (fold) in the activity (nLUC/fLUC) of M50 with respect to the wild-type FokI nuclease domain. The values are an average value and a standard error of three independent experiments. Here, * means a significant difference at P<0.1 and ** means a significant difference at P<0.05 from the reporter activity of the wild-type FokI effector.

The nuclease domain mutant (FokI nuclease domain mutant or homologous protein nuclease domain mutant) of the present invention has nuclease activity improved with the introduction of the mutation as compared with wild-type proteins. The nuclease activity is improved by preferably 10% or more, more preferably 30% or more, and further preferably 50% or more (for example, 70% or more, 100% or more, 150% or more, or 200% or more). The improvement of the nuclease activity can be evaluated by, for example, reporter assays to be described in Example 5 (FIGS. 4 and 5). Specifically, the improvement of the nuclease activity can be evaluated in such a way that: an effector plasmid which expresses a fusion protein of a nucleic acid binding domain such as TALEN or PPR and a nuclease domain mutant of the present invention, and a reporter plasmid which has a recognition sequence targeted by the nucleic acid binding domain, and which expresses the reporter when the fusion protein recognizes the recognition sequence and cleaves the DNA are introduced into cultured cells; and the reporter activity in the cultured cells is measured and compared with a case where a fusion protein containing a wild-type nuclease domain is expressed. This reporter assay system can use: HEK293-T cells, for example, as cultured cells; a CMV promoter, for example, as a promoter for promoting expression of the fusion protein or the reporter in each of the plasmids; and a recognition sequence on human B2M gene or GFP gene, for example, as the recognition sequence targeted by the nucleic acid binding domain.

The nuclease domain mutant of the present invention may contain a modified amino acid and/or unnatural amino acid. Modified amino acids include, but are not limited to, methylated amino acid, esterified amino acid, amidated amino acid, acetylated amino acid, alkylated amino acid, halogenated amino acid, and the like. The modified amino acid and the unnatural amino acid can be introduced by a known method.

<Artificial Nucleic Acid Cleaving Enzyme>

The present invention provides an artificial nucleic acid cleaving enzyme containing a nucleic acid binding domain and the aforementioned nuclease domain mutant. The artificial nucleic acid cleaving enzyme of the present invention is bound to a target sequence (recognition sequence targeted by the nucleic acid binding domain) on a nucleic acid via the nucleic acid binding domain, and cleaves the nucleic acid in the vicinity (target cleavage site) of the target sequence by the nuclease domain. Therefore, the artificial nucleic acid cleaving enzyme of the present invention is capable of functioning as a sequence-specific nucleic acid cleaving enzyme.

In the present specification, the "nucleic acid" covers both DNA and RNA. Nucleic acids to be cleaved by the artificial nucleic acid cleaving enzyme of the present invention are mainly DNAs. DNAs include both double-stranded DNAs and single-stranded DNAs. DNAs are not particularly limited, and examples thereof include eukaryotic nuclear genomic DNA, mitochondrial DNA, plastid DNA, prokaryotic genomic DNA, phage DNA, plasmid DNA, and the like. Preferably, the artificial nucleic acid cleaving enzyme of the present invention cleaves double-stranded DNA on the genome.

The target sequence for the artificial nucleic acid cleaving enzyme of the present invention is a certain sequence on a nucleic acid. In the case of targeting genomic DNA, the target sequence may be set in any gene region or extragenic region. The length of the target sequence is not particularly limited and is, for example, 10 to 30 bases. In the case of using a nucleic acid binding domain containing CRISPR/Cas, a sequence located in the vicinity of a proto-spacer adjacent motif (PAM) sequence is set as the target sequence because Cas needs to recognize the PAM sequence.

In the case where the artificial nucleic acid cleaving enzyme of the present invention cleaves double-strand DNA, it is preferable to set two target sequences flanking a spacer sequence. The length of the spacer sequence is not particularly limited, and is, for example, 1 to 20 bases. Those skilled in the art may set target sequences composed of desired base sequences with a desired length as appropriate. The two target sequences may be sequences palindromic with each other or may be non-palindromic sequences. In the case where the two target sequences are non-palindromic sequences, two types of artificial nucleic acid cleaving enzymes targeting the respective sequences are used.

The nucleic acid binding domain in the nucleic acid cleaving enzyme of the present invention may be any protein domain that is specifically bound to a certain nucleic acid sequence (target sequence) and examples thereof include zinc fingers, TALE, CRISPR/Cas (a complex of Cas protein and guide RNA), Pentatricopeptide repeat (PPR), and the like. In the artificial nucleic acid cleaving enzyme of the present invention, the nuclease domain mutant and the nucleic acid binding domain may be linked to each other directly or via a linker. The strand length of the linker is not particularly limited and is, for example, 1 to 20 amino acids.

A nucleic acid binding domain containing zinc fingers may preferably contain two or more zinc fingers, or may contain a zinc finger array including 3 to 9 zinc fingers as a non-limiting example. It is known that one zinc finger recognizes three consecutive bases. Accordingly, for example, a zinc finger array including 3 to 9 zinc fingers can recognize 9 to 27 bases. For examples of ZFNs, see a literature (International Publication No. WO2003/087341).

A nucleic acid binding domain containing TALE may preferably contain 6 or more repeat modules, or may contain TALE including 9 to 27 repeat modules as a non-limiting example. It is known that the repeat module has a repeat structure with 34 amino acids as one unit, and that one module recognizes one base. For examples of TALENs, see literatures (International Publication Nos. WO2012/104729, WO2011/072246 and WO2015/019672).

A nucleic acid binding domain containing PPR may preferably contain 6 or more repeat modules, or may contain PPR including 9 to 27 repeat modules as a non-limiting example. It is known that the repeat module has a repeat structure with 35 amino acids as one unit, and that one module recognizes one base. For examples of PPRs, see literatures (Nakamura et al., (2012) Plant Cell Physiol 53: 1171-1179 and International Publication No. WO2014/175284).

A nucleic acid binding domain containing CRISPR-Cas recognizes a target sequence with targeting RNA (crRNA) in guide RNA included in CRISPR-Cas. More specifically, the targeting RNA and the target sequence have base sequences complementary to each other and can be hybridized with each other. Since Cas forms a complex with the guide RNA, Cas is guided to the target sequence by the action of the guide RNA. In the present invention, a complex of guide RNA and Cas can be used as a nucleic acid binding domain. In this case, the nuclease mutant of the present invention is usually fused to Cas. In the present invention, since the nuclease mutant cleaves a nucleic acid, Cas in CRISPR/Cas does not necessarily have to retain nuclease activity. Preferably, Cas is Cas with inactivated nuclease activity (for example, dCas). The PAM recognition can be also altered by modifying Cas protein (for example, introducing a mutation) (Benjamin, P. et al., (2015) Nature 523: 481-485, Hirano, S. et al., (2016) Molecular Cell 61: 886-894, and International Publication No. WO2018/221685). In this way, a range of candidates for target sequences can be widened.

Examples of CRISPR/Cas used in the present invention include, but are not limited to, Class 2/Type II CRISPR/Cas such as CRISPR-Cas9, Class 2/Type V CRISPR/Cas such as CRISPR-Cpf1 (Cas12a), CRISPR-Cas12b, CRISPR-CasX (Cas12e), and CRISPR-Cas14, Class 2/Type VI CRISPR/Cas such as CRISPR-Cas13a, and Class 1/Type I CRISPR/Cas such as CRISPR-Cas3. For examples of CRISPR/Cas, see literatures (International Publication Nos. WO2014/093712, WO2013/176772, WO2013/142578, and WO2016/205711, Strecker J, et al., Nature Communications 10: 212 (2019), Liu J J, et al., Nature 566: 218-223 (2019), and International Publication No. WO2018/225858).

<Method for Producing Genome-Edited Cell or Non-human Organism>

The present invention provides a method for producing a genome-edited cell or non-human organism, comprising introducing, to the cell or the non-human organism, the above artificial nucleic acid cleaving enzyme, a polynucleotide encoding the artificial nucleic acid cleaving enzyme, or a vector containing the polynucleotide.

When the artificial nucleic acid cleaving enzyme of the present invention is introduced into a cell (including a cell in the body of a non-human organism), the nucleic acid binding domain is bound to a target sequence on a nucleic acid and the nuclease domain mutant cleaves the nucleic acid at a target cleavage site. Subsequent to this cleavage, a repair such as non-homologous end-joining repair (NHEJ) or homologous recombination repair (HR) is performed to edit the genome. In the repair by NHEJ, which is the main repair pathway, one or more mutations are inserted into the cleavage site to modify the nucleic acid. On the other hand, by using donor DNA to be described later, desired DNA in the donor DNA can be inserted into a target DNA region through a homologous recombination repair (HDR) occurring in a region around a target cleavage site.

The artificial nucleic acid cleaving enzyme of the present invention introduced into a cell may be in the form of protein, the form of a polynucleotide, or the form of a vector containing the polynucleotide. In the case where CRISPR-Cas is used as a nucleic acid binding domain of the artificial nucleic acid cleaving enzyme, the artificial nucleic acid cleaving enzyme may be further in the form of a complex of RNA and protein. The polynucleotide may be DNA or RNA, and may be codon-optimized for high expression in cells.

When the form of an expression vector is employed, the vector contains one or more regulatory elements operably bound to DNA to be expressed. The "operably bound" mentioned herein means that the above DNA is bound to the regulatory elements in a manner capable of being expressed. As the "regulatory elements", there are promoters, enhancers, internal ribosome entry sites (IRES), and other expression control elements (for example, transcription termination signals (for example, polyadenylation signals or poly U sequences)). Depending on the purpose, for example, the regulatory elements may direct constitutive expression of DNA in a wide variety of host cells or direct expression of DNA only in a specific cell, tissue, or organ. Instead, the regulatory elements may direct expression of DNA at a specific period of time, or direct expression of artificially inducible DNA. Examples of the promoters include polIII promoters (for example, U6 and H1 promoters), polII promoters (for example, retroviral Rous sarcoma virus (RSV) LTR promoter, cytomegalovirus (CMV) promoter, SV40 promoter, dihydrofolate reductase promoter, β-actin promoter, phospho glycerol kinase (PGK) promoter, and EF1α promoter), polI promoter, or a combination of them. Those skilled in the art can select an appropriate expression vector according to a type of cell targeted for introduction.

In the method for producing a genome-edited cell or non-human organism in the present invention, donor DNA may be introduced to the cell in addition to the above artificial nucleic acid cleaving enzyme. In this way, desired DNA can be inserted into the target DNA region by using a homologous recombination repair (HDR) occurring in the region around the target cleavage site. The process of a homologous recombination repair requires homology between the base sequence of the target DNA region and the base sequence of the donor DNA, uses the donor DNA in a template repair of the target DNA region containing the target cleavage site, and thereby transfers genetic information from the donor DNA to the target DNA region. This allows an alteration (for example, insertion, deletion, substitution, or the like) in the base sequence of the target DNA region. Therefore, the donor DNA contains two base sequences (homology arms) with high identity to the base sequences in the target DNA region and the desired DNA (DNA to be inserted into the target DNA region) flanked by them.

The homology arms only have to be long enough to allow homologous recombination. Although the length of the homology arms may vary depending on the form and strand length of donor DNA, the length ranges, for example, from 500 to 1000 base pairs for double-stranded donor DNA and, for example, from 30 to 1000 bases for single-stranded donor DNA. In addition, the homology arms do not necessarily have an identify of 100% to the base sequences in the target DNA region as long as the homology arms have the identity enough to carry out homologous recombination. For example, each of the homology arms has an identity of, for example, 95% or more, preferably 97% or more, more preferably 99% or more, and further preferably 99.9% or more.

The length of the desired DNA flanked by the homology arms is not particularly limited, and desired DNAs in various sizes can be used. If a base sequence desired to be removed afterwards exists in the desired DNA, for example, recombinant enzyme recognition sequences (for example, loxP sequences or FRT sequences) can be also added to both ends of the base sequence. The base sequence flanked by the recognition sequences can be removed by the action of the recombination enzyme (for example, Cre recombination enzyme or FLP recombination enzyme). Moreover, for the purpose of confirming success of DNA knock-in or the like, for example, a selection marker sequence (for example, fluorescent protein, drug resistance gene, or the like) can be also incorporated into the desired DNA. A gene operably bound to one or more regulatory elements can also be used as desired DNA.

The donor DNA may be linear DNA or circular DNA. Moreover, the donor DNA may be single-stranded DNA or double-stranded DNA.

The artificial nucleic acid cleaving enzyme of the present invention (in the above various forms) can be introduced into cells by a known method such, for example, as electroporation, microinjection, DEAE-dextran method, lipofection method, nanoparticle-mediated transfection method, or virus-mediated nucleic acid delivery method. In the case of direct administration into the body, parenteral administration such as injection and oral administration can be used. In this case, it is preferable to combine the artificial nucleic acid cleaving enzyme with a delivery system having directivity to the target site as needed. When donor DNA is used, the donor DNA can be introduced into cells or the body in the same method.

The cells to which the artificial nucleic acid cleaving enzyme of the present invention is to be introduced may be either cells of prokaryotes (prokaryotic cells) or cells of eukaryotes (eukaryotic cells), and are not particularly limited. Examples of the prokaryotic cells include Escherichia coli, actinomycetes, archaebacteria, and the like. Examples of the eukaryotic cells include animal cells, plant cells, algal cells, and fungal cells. Examples of the animal cells include mammalian cells, as well as cells of fishes, birds, reptiles, amphibians, and insects.

Examples of the animal cells include cells that make up an individual animal, cells that make up an organ or tissue isolated from an animal, cultured cells derived from animal tissue, and the like. Specific examples include: germ cells such as oocytes and sperms; embryonic cells of an embryo at each stage (for example, 1-cell stage embryo, 2-cell stage embryo, 4-cell stage embryo, 8-cell stage embryo, 16-cell stage embryo, morula stage embryo, or the like); stem cells such as induced pluripotent stem (iPS) cells and embryonic stem (ES) cells; somatic cells such as fibroblasts, hematopoietic cells, neurons, muscle cells, osteocytes, hepatocytes, pancreatic cells, brain cells, and kidney cells; and the like. As the oocytes for use to create a genome-edited animal, pre-fertilized and post-fertilized oocytes may be used, but preferable ones are post-fertilized oocytes, in other words, a fertilized egg. Particularly preferably, the fertilized egg is a pronuclear stage embryo. The cryopreserved oocytes can be used after thawing. However, application to human germ cells or embryonic cells is excluded if such application is not permissible from an ethical point of view.

The mammals are a concept covering humans and non-human mammals. Examples of the non-human mammals include even-toed ungulates such as cattle, wild boars, pigs, sheep, and goats; odd-toed ungulates animals such as horses; rodents such as mice, rats, guinea pigs, hamsters, and squirrels; lagomorpha such as rabbits; Carnivora such as dogs, cats, and ferrets; and the like. The non-human mammals may be domestic animals or companion animals (pet animals) or may be wild animals.

Examples of the plant cells include cells of cereals, oil crops, fodder crops, fruits, and vegetables. Examples of the plant cells include cells that make up an individual plant, cells that make up an organ or tissue isolated from a plant, cultured cells derived from plant tissue, and the like. Examples of the organ or tissue of a plant include leaves, stems, shoot apexes (growing points), roots, tubers, calluses, and the like. Examples of the plants include rice, corn, banana, peanut, sunflower, tomato, rapeseed, tobacco, wheat, barley, potato, soybean, cotton, carnation, and the like, and also include their propagation materials (for example, seeds, tuberous roots, tubers, and so on).

In the method for producing a genome-edited cell or non-human organism in the present invention, two or more types of the above artificial nucleic acid cleaving enzymes having different nucleic acid binding domains may be introduced into a cell. For example, if no palindromic sequences are present in a region desired to be edited on the genome, two types of artificial nucleolytic enzymes targeting different sequences may be used. In this case, further mutations to promote heterodimerization of the nuclease domain mutants of the two types of artificial nucleic acid cleaving enzymes may be introduced into the nuclease domain mutants. In this way, it is possible to increase the number of recognition sequences targeted by the artificial nucleic acid cleaving enzymes and reduce the off-target probability.

<Kit>

The present invention provides a kit for genome editing of a cell or organism, containing the above artificial nucleic acid cleaving enzyme, a polynucleotide encoding the artificial nucleic acid cleaving enzyme, or a vector containing the polynucleotide. The kit may further contain one or more additional reagents and examples of the additional reagents include, but are not limited to, dilution buffer, reconstitution solution, washing buffer, nucleic acid transfer reagent, protein delivery reagent, and control reagent. In general, the kit is accompanied by an instruction manual.

EXAMPLES

Example 1. Principle of B2P Screening

A B2P screening system uses two plasmids which are a reporter plasmid carrying a lethal gene named the ccdB gene and an effector plasmid for expressing TALEN-A (Chen Z, Zhao H. (2005) Nucleic Acids Res. 33: e154). Downstream of the ccdB gene in the reporter plasmid, sequences to be recognized by TALEN-A (Table 1) are inserted on a sense strand side and an antisense strand side, respectively ("target sequence-spacer sequence-sequence complementary to the target sequence" are arrayed when seen from the sense strand side) (Table 2). In Table 2, upper-case letters indicate sequences to be recognized by TALEN-A, and lower-case letters indicate a spacer sequence flanked by the two sequences.

TABLE 1

| Name | Target Sequence |
| --- | --- |
| TALEN-A | AGCCGAAATCATCGCAG (SEQ ID NO: 3) |
| GFP_TALEN(L) | CAGCGTGTCCGGCGA (SEQ ID NO: 4) |
| GFP_TALEN(R) | TTGCCGTAGGTGGCA (SEQ ID NO: 5) |
| B2M_TALEN(L) | CCAAAGATTCAGGT (SEQ ID NO: 6) |
| B2M_TALEN(R) | GACTTTCCATTCTC (SEQ ID NO: 7) |

TABLE 2

| Name | Sequence |
| --- | --- |
| TALEN-A | AGCCGAAATCATCGCAGccgctgccgcgagctcCTGCGAT GATTTCGGCT (SEQ ID NO: 8) |
| GFP_TALEN | CAGCGTGTCCGGCGAGgggagggcgaTGCCACCT (SEQ ID NO: 9) |
| B2M_TALEN | CCAAAGATTCAGGTttactcacgtcatccagcaGAGAAT C (SBQ ID NO: 10) |

The expression of the ccdB gene can be controlled by an arabinose-inducible promoter, and *Escherichia coli* transformed with the reporter cannot survive in a medium supplemented with arabinose (this plasmid is referred to as "TALEN-A reporter plasmid"). In the effector plasmid, TALEN-A is fused with maltose-binding protein at the N-terminal side, and is capable of inducing MBP-TALEN-A fusion protein with IPTG (this plasmid is referred to as "TALEN-A effector plasmid"). When these two types of plasmids are transformed into *Escherichia coli* (XL1-Blue), the transformant cannot not survive in the presence of arabinose, but can survive in the presence of arabinose and IPTG. This is because MBP-TALEN-A introduces a double-stranded DNA break into the target sequence in the TALEN-A reporter plasmid, which disables DNA replication of the cut plasmid DNA and makes the reporter plasmid disappear from the transformant, so that the lethal effect of the ccdB gene is lost. When a TALEN-A effector mutant library is introduced into *Escherichia coli* harboring the TALEN-A reporter and screening is performed in the presence of arabinose and IPTG, *Escherichia coli* harboring the TALEN-A effector with the high activity can survive, but *Escherichia coli* harboring the TALEN-A effector with the weak activity cannot survive. The TALEN-A effector plasmid DNA is extracted from the surviving *Escherichia coli* and transformed into *Escherichia coli* harboring the TALEN-A reporter again, so that *Escherichia coli* harboring the TALEN-A effector with the highest activity are further enriched. By repeating the above cycles, the plasmid containing the TALEN-A effector with the highest activity can be isolated.

Example 2. Construction of Mutant Library

The TALEN-A effector mutant library was constructed in the following way. A destination vector was constructed by PCR-amplifying TALEN-A effector plasmid DNA as a template using PrimeSTAR (registered trademark) HS DNA Polymerase (TaKaRa), removing the FokI-CD portion, and introducing an Esp3I site. By using GeneMorph II Random Mutagenesis kit (Agilent Technologies), an insert was prepared in which the base sequence of the FokI-CD portion of the MBP-TALEN-A gene was amplified and random mutations were introduced into the base sequence of the FokI-CD. The TALEN-A effector mutant library was constructed by ligating the destination vector cleaved by Esp3I and the insert. Evaluation of the introduction rate of random mutations revealed that four base substitutions on average were introduced into the base sequence (595 bp) of the FokI-CD portion.

Example 3. Screening of Mutant Library

In the first screening of stage 1, 1 μg of plasmid DNA of the constructed mutant library was transformed into *Escherichia coli* harboring the TALEN-A reporter by the electroporation method (Bio-Rad). After the electroporation, the *Escherichia coli* were transferred into 30 mL of SOB, followed by recovery culture at 37° C. for 1 hour. IPTG was added to a final concentration of 1 mM, followed by incubation at 30° C. for 4 hours, and then the resultant bacterial solution was plated on an LB agar plate containing 100 mg/L chloramphenicol (Cm) and 0.2% arabinose. At this time, a portion of the bacterial solution was plated on each of LB+Cm agar plates supplemented with and without arabinose, and the survival rate was determined by comparing the numbers of colonies. The total number of colonies in the first screening was $2 \times 10^7$, whereas the number of colonies obtained on the medium with arabinose was $6 \times 10^6$. Therefore, the survival rate was 30%. The colonies on the medium with arabinose were suspended in an SOB medium, and plasmid DNA was extracted from the bacterial solution using NucleoSpin (registered trademark) Plasmid (TaKaRa).

The second screening was performed by using the extracted plasmid DNA in the same manner as in the first screening. In this screening, the total number of colonies was $6.8 \times 10^8$ and the survive rate was 58%. In the third screening, the survive rate was 100%. Since better TALEN-A effector could not be selected under the above conditions, the selection conditions in the fourth screening were made stricter by shortening the induction time with IPTG from 4 hours to 2 hours. The survive rate was 20% in the fourth screening, but the survive rate reached 90% in the fifth screening performed under the same conditions. In the sixth to eighth screenings, the induction time with IPTG was set to one hour, and the survive rates were 1.3%, 10%, and 6.5%, respectively. The survival rate did not improve even though the screenings were repeated, and the number of independent clones calculated from $6\times10^6$, which was the number of independent clones in the first screening, and the survival rates in the eight screenings was 55 or less. For these reasons, the stage 1 was ended at the end of the eighth screening.

A mutation-reintroduced library was constructed by using the plasmid DNA obtained in the 8th screening of the stage 1 as a template and inserting, into the destination vector, a FokI-CD insert in which random mutations were further introduced. This library was transformed into *Escherichia coli* harboring the TALEN-A reporter and screenings of stage 2 were started. The stage 2 was performed with induction with 1 mM IPTG for one hour in the first screening, for 30 minutes in the second and third screenings, and for 15 minutes in the fourth screening, and then with induction with 0.1 mM IPTG for 15 minutes in the fifth and sixth screenings. The induction was performed at 30° C. in the first screening, and then at 37° C. in the second and following screenings. The number of independent clones calculated from $2.8\times10^5$, which is the number of independent clones in the first screening, and the survival rates in the six screenings was 1.

A mutation-reintroduced library was constructed by using the plasmid DNA obtained in the sixth screening of the stage 2 as a template and inserting, into the destination vector, a FokI-CD insert in which random mutations were further introduced. This library was transformed into *Escherichia coli* harboring the TALEN-A reporter and screenings of stage 3 were started. In the stage 3, induction for 15 minutes was conducted with 20 µM of IPTG in the first screening, with 10 µM of IPTG in the second and third screenings, with 1 µM of IPTG in the fourth screening, and then with no IPTG in the fifth and sixth screenings. The induction was conducted at 30° C. in the first screening, and then at 37° C. in the second and following screenings. Since the number of independent clones calculated from $1.5\times10^5$, which is the number of independent clones in the first screening, and the survival rates in the six screenings was 1, the screenings of the stage 3 were ended.

A mutation-reintroduced library was constructed by using the plasmid DNA obtained in the sixth screening of the stage 3 as a template and inserting, into the destination vector, a FokI-CD insert in which random mutations were further introduced. This library was transformed into *Escherichia coli* harboring the TALEN-A reporter and screenings of stage 4 were started. Five screenings were performed under the same conditions (with induction for 5 minutes at 37° C. in the presence of 0.5 µM of IPTG). Since the number of independent clones calculated from $8.0\times10^4$, which is the number of independent clones in the first screening, and the survival rates in the six screenings was 6, the screenings of the stage 4 were ended.

In the stage 4, plasmid DNAs were extracted from colonies obtained by transforming *Escherichia coli* XL1Blue strain with the plasmid DNA obtained in the fifth screening, and the base sequences of the FokI-CD portions were checked. As a result, four mutant types FokI (M47, M48, M49, and M50) were obtained. Each of M47, M48, and M49 had 10 amino acid substitutions, whereas M50 had 11 amino acid substitutions (FIG. 1).

The amino acid substitutions found in the four mutant types FokI isolated were compared with the amino acid substitutions in an existing mutant type FokI. The Sharkey variant that exhibits high activity in zinc finger nucleases includes the S418P and K441E substitutions (NPL 2 listed above). In M48, the S418P substitution is present but the K441E substitution is not present. NPL 2 also verifies the effect of the Q481H and N527D mutations, but their effect is smaller than that of the Sharkey variant. The Q481H substitution is also present in M50. In addition, heterodimerization mutations, Q486E/I499L/N496D and E490K/I538K/H537R, in which FokI dimerizes only different molecules, have been reported (Doyon Y, et al., (2011) Nat Methods. 8: 74-79). The substitutions were introduced at Q486 in M47, M48 and M49, in which the Q486L substitution was found in M47 and M49, and the Q486H substitution was found in M48. The E490Q substitution is present in M50, which differs from the E490K substitution in Literature of Doyon et al. Although similar heterodimerization mutations have been also reported in Literatures (Ramalingam S, et al., (2011) J Mol Biol. 405: 630-641, and Szczepek M, et al., (2007) Nat Biotechnol. 25: 786-793), there are no common amino acid substitutions other than the residues common to the literature of Doyon et al. and the four types of mutants isolated in the present Example. Although the Q481A substitution has been reported as a mutation that reduces off-target mutations (Miller J C, et al., (2019) Nat Biotechnol. 37: 945-952), this Q481A substitution is different from the Q486L substitution found in M47 and M49 and the Q486H substitution found in M48.

Example 4. Evaluation of Mutant Types FokI Using *Escherichia Coli* B2P (1) First, how much the survival rate of each of the four mutant types FokI (M47, M48, M49, and M50) was increased compared to a wild-type FokI was checked using *Escherichia coli* B2P. First, 10 ng of TALEN-A effector plasmid DNA containing each of the wild-type FokI and the four mutant types FokI (M47, M48, M49, and M50) was transformed into *Escherichia coli* harboring the TALEN-A reporter by the electroporation method (Bio-Rad). After recovery culture at 37° C. for 1 hour with addition of 1 mL of SOB, TALEN-A was induced by incubation at 37° C. for 15 minutes with addition of 6 mL of SOB containing 0.1 mM IPTG. The transformant was plated on plates supplemented with and without arabinose and cultured overnight at 37° C. and thereafter the number of colonies was counted. The survival rate was defined as a value obtained by dividing the number of colonies on the arabinose-supplemented plate by the number of colonies on the non-arabinose-supplemented plate.

As a result, the survival rate of the TALEN-A effector-expressing *Escherichia coli* having the wild-type FokI was 0.0001%, whereas the survival rate of the *Escherichia coli* using M47, M48, M49, or M50 as FokI was 29%, 37%, 45%, or 28%, respectively (FIG. 2). The mutant types FokI-TALEN-A effectors achieved the increased activity that was 210,000-fold (M47 and M50) to 330,000-fold (M49) higher than that of the wild-type.

(2) Among the four mutant types FokI (M47, M48, M49, and M50), M48 and M50 have the G473R mutation in common. The G473R mutation is a mutation already identified in the first stage (Stage 1) of the screenings, and neighbors the K469 residue, which is the active center of FokI nuclease. Therefore, the importance of the G473R mutation on the nuclease activity of M50 was examined by using *Escherichia coli* B2P. First, a TALEN-A effector plasmid was constructed in which a reverse mutation (M50(G473)) for restoring the G473 residue of the wild-type from the R473 residue of M50 was introduced by a PCR method. Then, 10 ng of the TALEN-A effector plasmid DNA containing each of the wild-type FokI, M50, and M50(G473) was transformed into *Escherichia coli* harboring the TALEN-A reporter by the electroporation method (Bio-Rad). After recovery culture at 37° C. for 1 hour with addition of 1 mL of SOB, TALEN-A was induced by incubation at 37° C. for 15 minutes with addition of 6 mL of SOB containing 0.1 mM IPTG. The transformant was plated on plates supplemented with and without arabinose and cultured overnight at 37° C. and thereafter the number of colonies was counted. The survival rate was defined as a value obtained by dividing the number of colonies on the arabinose-supplemented plate by the number of colonies on the non-arabinose-supplemented plate.

Figure 3:
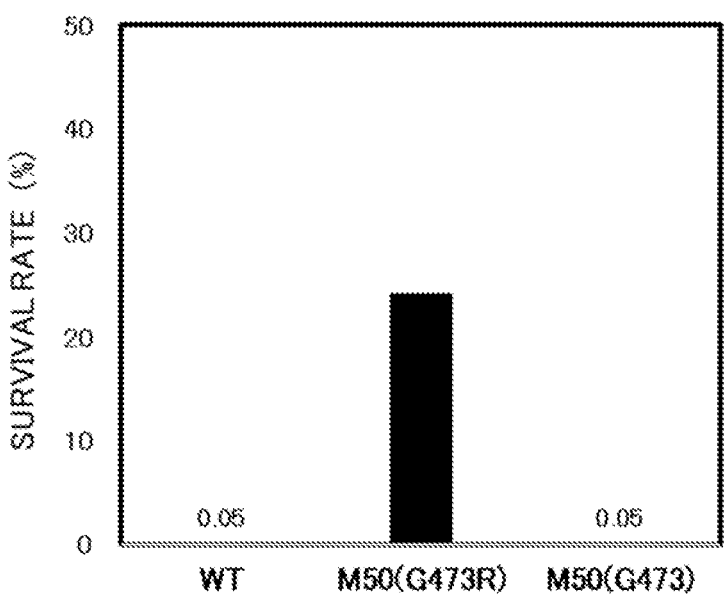
FIG. 3 is a diagram presenting results of evaluating the effect of a G473R mutation in the FokI nuclease domain on the nuclease activity, using, as an index, a survival rate in an artificial evolution system (B2P) of *Escherichia coli*. The survival rate is a value obtained by dividing the number of colonies on an arabinose-supplemented plate by the number of colonies on a non-arabinose-supplemented plate. WT is a wild-type FokI nuclease domain fused with a TALEN-A effector. The numeric values in the diagram are the survival rates in the case of using the wild-type FokI nuclease domain and the case of using M50 (M50 (G473)) with a G473 reverse mutation introduced.

As a result, the survival rate of the TALEN-A effector-expressing *Escherichia coli* containing M50 was 24%, whereas the survival rate of the TALEN-A effector-expressing *Escherichia coli* containing M50(G473) was 0.05% or less (FIG. 3). This revealed the importance of the G473R mutation on the nuclease activity of M50.

Example 5. Evaluation of Mutant Types FokI by Reporter Assays in Cultured Animal Cells (1) Subsequently, in order to examine whether the mutant types FokI improved genome editing efficiency, the performance of an effector with each of the mutant types FokI linked to TALE was evaluated by using a single strand annealing (SSA) reporter, which is used as a standard method for evaluating genome editing efficiency.

Human codon-optimized genes were synthesized for the purpose of enabling efficient expression of the four mutant types FokI (M47, M48, M49, and M50) in animal cells. An effector plasmid for animal cells was constructed by fusing each of the four human codon-optimized mutant types FokI-CD to the C-terminal side of TALEN targeting the human GFP gene (GFP_TALEN) or TALEN targeting the human B2M gene (B2M_TALEN), and then inserting the resultant into an expression vector with a CMV promoter using a Golden-Gate method. The sequences to be recognized by the TALENs used are presented in the above Table 1.

The SSA reporter having each of the target sequences to be recognized by the above TALENs has the following structure. Downstream of the CMV promoter, a 5'-side 1131 bp sequence of firefly luciferase (fLUC), the target sequence, and a 3'-side 1317 bp sequence of fLUC were linked in this order. Here, fLUC has 795 bp overlapping sequences on the 5' and 3' sides, and normal fLUC is produced and expressed when homologous recombination occurs between these overlapping sequences. The target sequences are presented in the above Table 2.

The SSA reporter assay was conducted in the following way. First, 1500 human cultured cells, HEK293-T cells were pre-cultured for 1 day and were transfected with 2.0 ng of the reporter plasmid DNA, 10 ng of the effector plasmid DNA, and 0.5 ng of reference plasmid DNA by using FuGENE (registered trademark) Transfection Reagent (Promega). After cultivation at 37° C. for 2 days in the presence of 5% $CO_2$, the activity of fLUC and rLUC was measured by using Dual-Glo (registered trademark) Luciferase Assay System (Promega). Each sample was assayed in quadruplicate three times. As a result, all the four mutant types FokI demonstrated the higher activity than that of the wild-type (FIG. 4).

(2) Whether the mutant type FokI improves genome editing efficiency even when used with PPRs was examined by using Fn (Firefly luciferase & NanoLUC) reporter that can detect genome editing with high sensitivity.

An effector plasmid for animal cells was constructed by fusing human codon-optimized wild-type FokI or M50 to the C terminal sides of a pair of PPRs targeting the human B2M gene or GFP gene (B2M_PPRs or GFP PPRs), and then inserting the resultant into an expression vector with a CMV promoter. Here, sequences to be recognized by the PPRs used are presented in Table 3.

TABLE 3

| Name | Target Sequence |
|------|-----------------|
| B2M_PPR (L) | AATGGAAAGTCAAA (SEQ ID NO: 15) |
| B2M_PPR (R) | AGCAATTCAGGAAA (SEQ ID NO: 16) |
| GEP_PPR (L) | ACGACTTCTTCAAGT (SEQ ID NO: 17) |
| GEP_PPR (R) | CCTGGACGTAGCCTT (SEQ ID NO: 18) |

An Fn reporter having each of the target sequences to be recognized by the above PPRs has the following structure. The Fn reporter plasmid was construct by linking firefly luciferase (fLUC), the target sequence, and NanoLuc (nLUC) in this order downstream of the CMV promoter. In the Fn reporter system, fLUC and the target sequence are linked in-frame. For this reason, usually, the sequence up to fLUC is translated, but nLUC is not translated because a stop codon exists upstream of nLUC. Therefore, the activity of fLUC alone is detected usually. On the other hand, when the target sequence is edited to generate an indel, a frameshift occurs in the target sequence, and a reporter gene in which fLUC and nLUC are fused is expressed, so that the activity of both fLUC and nLUC is detected. Table 4 presents the target sequences of the human B2M gene and the GFP gene inserted into the Fn reporter systems.

TABLE 4

| Name | Sequence |
|------|----------|
| B2M Target | TACTCCAAAGATTCAGGTTTACTCACGTCATCCAGCAGAGAAT GGAAAGTCAAATTTCCTGAATTGCTATGTGTCTGGGTTTCATC CATCCGACAT (SEQ ID NO: 19) |
| GFP Target | CAAGTTCAGCGTGTCCGGCGAGGGCGAGGGCGATGCCACCTAC GGCAAGCTGACCCTGAAGTTCATCTGCACCACCGGCAAGCTGC CCGTGCCCTGGCCCACCCTCGTGACCACCCTGACCTACGGCGT GCAGTGCTTCAGCCGCTACCCCGACCACATGAAGCAGCACGAC TTCTTCAAGTCCGCCATGCCCGAAGGCTACGTCCAGGAGC (SEQ ID NO: 20) |

The Fn reporter assay was conducted in the following way. First, 1500 human cultured cells, HEK293-T cells were pre-cultured for 1 day. The pre-cultured HEK293-T cells were transfected with 2.5 ng of the Fn reporter plasmid DNA and 50 ng of the effector plasmid DNA for each of PPR(L) and PPR(R) by using FuGENE (registered trademark) Transfection Reagent (Promega). After cultivation at 37° C. overnight in the presence of 5% $CO_2$, the activity of fLUC and nLUC was measured by using Nano-Glo (registered trademark) Luciferase Assay System (Promega). Each sample was assayed in quadruplicate and the activity was evaluated with a value obtained by dividing nLUC by fLUC.

As a result, M50 exhibited the activity 2.2-fold higher than that of the wild-type FokI when targeting the B2M gene, and the activity 1.5-fold higher than that of the wild-type FokI when targeting the GFP gene (FIG. 5). The above results revealed that M50 exhibits higher performance than that of the wild-type FokI even when linked to PPRs.

INDUSTRIAL APPLICABILITY

As described above, the novel nuclease domain mutants of the invention have activity superior to that of the wild-type FokI nuclease domain in combination with various nucleic acid binding domains. The artificial nucleic acid cleaving enzyme of the present invention is useful as genome editing tools not only for basic research but also for various industrial applications including medicine, agriculture, and industry.

SEQUENCE LISTING FREE TEXT

SEQ ID NO: 3
<223> Target Sequence of TALEN-A
SEQ ID NO: 4
<223> Target Sequence of GFP_TALEN(L)

SEQ ID NO: 5
<223> Target Sequence of GFP_TALEN(R)
SEQ ID NO: 6
<223> Target Sequence of B2M_TALEN(L)
SEQ ID NO: 7
<223> Target Sequence of B2M_TALEN(R)
SEQ ID NO: 8
<223> Target Site of TALEN-A
SEQ ID NO: 9
<223> Target Site of GFP_TALEN
SEQ ID NO: 10
<223> Target Site of B2M_TALEN
SEQ ID NO: 11
<223> M47 Mutant
SEQ ID NO: 12
<223> M48 Mutant
SEQ ID NO: 13
<223> M49 Mutant
SEQ ID NO: 14
<223> M50 Mutant
SEQ ID NO: 15
<223> Target Sequence of B2M_PPR(L)
SEQ ID NO: 16
<223> Target Sequence of B2M_PPR(R)
SEQ ID NO: 17
<223> Target Sequence of GFP_PPR(L)
SEQ ID NO: 18
<223> Target Sequence of GFP_PPR(R)
SEQ ID NO: 19
<223> Target Site of B2M_PPR
SEQ ID NO: 20
<223> Target Site of GFP_PPR

The invention claimed is:

1. A nuclease domain mutant of a FokI protein, comprising the amino acid sequence set forth in SEQ ID NO: 11, 12, 13, or 14.

2. An artificial nucleic acid cleaving enzyme comprising a nucleic acid binding domain and the nuclease domain mutant according to claim 1.

3. The artificial nucleic acid cleaving enzyme according to claim 2, wherein the nucleic acid binding domain is TALE (transcription activator-like effector), zinc finger, PPR (pentatricopeptide repeat), or CRISPR (Clustered Regularly Interspaced Short Palindromic Repeats)-Cas.

4. A polynucleotide encoding (a) the nuclease domain mutant according to claim 1 or (b) an artificial nucleic acid cleaving enzyme comprising a nucleic acid binding domain and the nuclease domain mutant according to claim 1.

5. A vector comprising the polynucleotide according to claim 4.

6. A cell comprising the polynucleotide according to claim 4 or the vector according to claim 5.

7. A method for producing a genome-edited cell or non-human organism, comprising introducing, to the cell or the non-human organism, the artificial nucleic acid cleaving enzyme according to claim 2, a polynucleotide encoding the artificial nucleic acid cleaving enzyme, or a vector containing the polynucleotide.

8. A kit for genome editing of a cell or organism, comprising the artificial nucleic acid cleaving enzyme according to claim 2, a polynucleotide encoding the artificial nucleic acid cleaving enzyme, or a vector containing the polynucleotide.

\* \* \* \* \*

```
SEQUENCE LISTING

<160> NUMBER OF SEQ ID NOS: 20

<210> SEQ ID NO 1
<211> LENGTH: 579
<212> TYPE: PRT
<213> ORGANISM: Flavobacterium okeanokoites

<400> SEQUENCE: 1

Met Val Ser Lys Ile Arg Thr Phe Gly Trp Val Gln Asn Pro Gly Lys
1               5                   10                  15

Phe Glu Asn Leu Lys Arg Val Val Gln Val Phe Asp Arg Asn Ser Lys
            20                  25                  30

Val His Asn Glu Val Lys Asn Ile Lys Ile Pro Thr Leu Val Lys Glu
        35                  40                  45

Ser Lys Ile Gln Lys Glu Leu Val Ala Ile Met Asn Gln His Asp Leu
    50                  55                  60

Ile Tyr Thr Tyr Lys Glu Leu Val Gly Thr Gly Thr Ser Ile Arg Ser
65                  70                  75                  80

Glu Ala Pro Cys Asp Ala Ile Ile Gln Ala Thr Ile Ala Asp Gln Gly
                85                  90                  95

Asn Lys Lys Gly Tyr Ile Asp Asn Trp Ser Ser Asp Gly Phe Leu Arg
            100                 105                 110

Trp Ala His Ala Leu Gly Phe Ile Glu Tyr Ile Asn Lys Ser Asp Ser
            115                 120                 125

Phe Val Ile Thr Asp Val Gly Leu Ala Tyr Ser Lys Ser Ala Asp Gly
    130                 135                 140

Ser Ala Ile Glu Lys Glu Ile Leu Ile Glu Ala Ile Ser Ser Tyr Pro
```

-continued

```
145               150               155               160

Pro Ala Ile Arg Ile Leu Thr Leu Leu Glu Asp Gly Gln His Leu Thr
                165               170               175

Lys Phe Asp Leu Gly Lys Asn Leu Gly Phe Ser Gly Glu Ser Gly Phe
                180               185               190

Thr Ser Leu Pro Glu Gly Ile Leu Leu Asp Thr Leu Ala Asn Ala Met
        195               200               205

Pro Lys Asp Lys Gly Glu Ile Arg Asn Asn Trp Glu Gly Ser Ser Asp
        210               215               220

Lys Tyr Ala Arg Met Ile Gly Gly Trp Leu Asp Lys Leu Gly Leu Val
225               230               235               240

Lys Gln Gly Lys Lys Glu Phe Ile Ile Pro Thr Leu Gly Lys Pro Asp
                245               250               255

Asn Lys Glu Phe Ile Ser His Ala Phe Lys Ile Thr Gly Glu Gly Leu
                260               265               270

Lys Val Leu Arg Arg Ala Lys Gly Ser Thr Lys Phe Thr Arg Val Pro
        275               280               285

Lys Arg Val Tyr Trp Glu Met Leu Ala Thr Asn Leu Thr Asp Lys Glu
        290               295               300

Tyr Val Arg Thr Arg Arg Ala Leu Ile Leu Glu Ile Leu Ile Lys Ala
305               310               315               320

Gly Ser Leu Lys Ile Glu Gln Ile Gln Asp Asn Leu Lys Lys Leu Gly
                325               330               335

Phe Asp Glu Val Ile Glu Thr Ile Glu Asn Asp Ile Lys Gly Leu Ile
                340               345               350

Asn Thr Gly Ile Phe Ile Glu Ile Lys Gly Arg Phe Tyr Gln Leu Lys
        355               360               365

Asp His Ile Leu Gln Phe Val Ile Pro Asn Arg Gly Val Thr Lys Gln
        370               375               380

Leu Val Lys Ser Glu Leu Glu Glu Lys Lys Ser Glu Leu Arg His Lys
385               390               395               400

Leu Lys Tyr Val Pro His Glu Tyr Ile Glu Leu Ile Glu Ile Ala Arg
                405               410               415

Asn Ser Thr Gln Asp Arg Ile Leu Glu Met Lys Val Met Glu Phe Phe
                420               425               430

Met Lys Val Tyr Gly Tyr Arg Gly Lys His Leu Gly Gly Ser Arg Lys
                435               440               445

Pro Asp Gly Ala Ile Tyr Thr Val Gly Ser Pro Ile Asp Tyr Gly Val
        450               455               460

Ile Val Asp Thr Lys Ala Tyr Ser Gly Gly Tyr Asn Leu Pro Ile Gly
465               470               475               480

Gln Ala Asp Glu Met Gln Arg Tyr Val Glu Glu Asn Gln Thr Arg Asn
                485               490               495

Lys His Ile Asn Pro Asn Glu Trp Trp Lys Val Tyr Pro Ser Ser Val
                500               505               510

Thr Glu Phe Lys Phe Leu Phe Val Ser Gly His Phe Lys Gly Asn Tyr
        515               520               525

Lys Ala Gln Leu Thr Arg Leu Asn His Ile Thr Asn Cys Asn Gly Ala
        530               535               540

Val Leu Ser Val Glu Glu Leu Leu Ile Gly Gly Glu Met Ile Lys Ala
545               550               555               560

Gly Thr Leu Thr Leu Glu Glu Val Arg Arg Lys Phe Asn Asn Gly Glu
                565               570               575
```

Ile Asn Phe

<210> SEQ ID NO 2
<211> LENGTH: 196
<212> TYPE: PRT
<213> ORGANISM: Flavobacterium okeanokoites

<400> SEQUENCE: 2

```
Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Ser Thr Gln Asp Arg Ile Leu Glu Met Lys Val Met Glu Phe
        35                  40                  45

Phe Met Lys Val Tyr Gly Tyr Arg Gly Lys His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Gln Arg Tyr Val Glu Glu Asn Gln Thr Arg
            100                 105                 110

Asn Lys His Ile Asn Pro Asn Glu Trp Trp Lys Val Tyr Pro Ser Ser
            115                 120                 125

Val Thr Glu Phe Lys Phe Leu Phe Val Ser Gly His Phe Lys Gly Asn
    130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
        195
```

<210> SEQ ID NO 3
<211> LENGTH: 17
<212> TYPE: DNA
<213> ORGANISM: Artificial Sequence
<220> FEATURE:
<223> OTHER INFORMATION: Target Sequence of TALEN-A

<400> SEQUENCE: 3
agccgaaatc atcgcag      17

<210> SEQ ID NO 4
<211> LENGTH: 15
<212> TYPE: DNA
<213> ORGANISM: Artificial Sequence
<220> FEATURE:
<223> OTHER INFORMATION: Target Sequence of GFP_TALEN(L)

<400> SEQUENCE: 4
cagcgtgtcc ggcga      15

<210> SEQ ID NO 5
<211> LENGTH: 15
<212> TYPE: DNA
<213> ORGANISM: Artificial Sequence

```
<220> FEATURE:
<223> OTHER INFORMATION: Target Sequence of GFP_TALEN(R)

<400> SEQUENCE: 5
ttgccgtagg tggca                                                      15

<210> SEQ ID NO 6
<211> LENGTH: 14
<212> TYPE: DNA
<213> ORGANISM: Artificial Sequence
<220> FEATURE:
<223> OTHER INFORMATION: Target Sequence of B2M_TALEN(L)

<400> SEQUENCE: 6
ccaaagattc aggt                                                       14

<210> SEQ ID NO 7
<211> LENGTH: 14
<212> TYPE: DNA
<213> ORGANISM: Artificial Sequence
<220> FEATURE:
<223> OTHER INFORMATION: Target Sequence of B2M_TALEN(R)

<400> SEQUENCE: 7
gactttccat tctc                                                       14

<210> SEQ ID NO 8
<211> LENGTH: 50
<212> TYPE: DNA
<213> ORGANISM: Artificial Sequence
<220> FEATURE:
<223> OTHER INFORMATION: Target Site of TALEN-A

<400> SEQUENCE: 8
agccgaaatc atcgcagccg ctgccgcgag ctcctgcgat gatttcggct               50

<210> SEQ ID NO 9
<211> LENGTH: 42
<212> TYPE: DNA
<213> ORGANISM: Artificial Sequence
<220> FEATURE:
<223> OTHER INFORMATION: Target Site of GFP_TALEN

<400> SEQUENCE: 9
cagcgtgtcc ggcgagggcg agggcgatgc cacctacggc aa                       42

<210> SEQ ID NO 10
<211> LENGTH: 47
<212> TYPE: DNA
<213> ORGANISM: Artificial Sequence
<220> FEATURE:
<223> OTHER INFORMATION: Target Site of B2M_TALEN

<400> SEQUENCE: 10
ccaaagattc aggtttactc acgtcatcca gcagagaatg gaaagtc                  47

<210> SEQ ID NO 11
<211> LENGTH: 196
<212> TYPE: PRT
<213> ORGANISM: Artificial Sequence
<220> FEATURE:
<223> OTHER INFORMATION: M47 mutant

<400> SEQUENCE: 11

Gln Leu Met Lys Ser Glu Leu Glu Glu Lys Lys Ser Glu Leu Arg Arg
1               5                   10                  15
```

-continued

```
Lys Leu Lys Tyr Val Pro His Glu Tyr Ile Glu Leu Ile Glu Ile Ala
            20                  25                  30

Arg Asn Ser Thr Gln Tyr Arg Ile Phe Glu Met Lys Val Met Glu Phe
            35                  40                  45

Leu Val Lys Val Tyr Gly Tyr Arg Gly Lys His Leu Gly Gly Ser Arg
        50                  55                  60

Asn Pro Asp Gly Ala Ile Tyr Thr Val Gly Ser Pro Ile Asp Tyr Gly
65                  70                  75                  80

Val Ile Ile Asp Thr Lys Ala Tyr Ser Gly Gly Tyr Asn Leu Pro Ile
                85                  90                  95

Gly Gln Ala Asp Ala Met Leu Arg Tyr Val Glu Glu Asn Gln Thr Arg
                100                 105                 110

Asn Lys His Ile Asn Pro Asn Glu Trp Trp Lys Val Tyr Pro Ser Ser
            115                 120                 125

Val Thr Glu Phe Lys Phe Leu Phe Val Ser Gly His Phe Lys Gly Asn
        130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
                180                 185                 190

Glu Ile Asn Phe
            195
```

```
<210> SEQ ID NO 12
<211> LENGTH: 196
<212> TYPE: PRT
<213> ORGANISM: Artificial Sequence
<220> FEATURE:
<223> OTHER INFORMATION: M48 mutant

<400> SEQUENCE: 12

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Pro Thr Leu Asp Arg Ile Leu Glu Met Lys Val Met Glu Phe
            35                  40                  45

Phe Met Lys Val Tyr Gly Tyr Arg Gly Lys His Leu Gly Gly Ser Arg
        50                  55                  60

Lys Pro Asp Gly Val Ile Tyr Thr Val Gly Ser Pro Ile Asp Tyr Gly
65                  70                  75                  80

Val Ile Val Asp Thr Lys Ala Tyr Ser Arg Gly Tyr Asn Leu Pro Ile
                85                  90                  95

Gly Gln Ala Asp Glu Met His Arg Tyr Val Val Glu Asn Gln Thr Arg
                100                 105                 110

Asn Lys Leu Ile Asn Pro Asn Glu Trp Trp Lys Val Tyr Pro Ser Ser
            115                 120                 125

Val Thr Glu Phe Lys Phe Leu Phe Val Ser Gly His Phe Lys Gly Asn
        130                 135                 140

Tyr Lys Ala Gln Leu Thr Arg Leu Asn His Ile Thr Asn Cys Lys Gly
145                 150                 155                 160

Ala Val Leu Ser Val Glu Glu Leu Leu Ile Gly Gly Glu Met Ile Arg
                165                 170                 175
```

```
Ala Gly Thr Leu Thr Leu Glu Glu Val Arg Ser Lys Phe Asn Asn Gly
            180                 185                 190

Glu Ile Asn Phe
        195

<210> SEQ ID NO 13
<211> LENGTH: 196
<212> TYPE: PRT
<213> ORGANISM: Artificial Sequence
<220> FEATURE:
<223> OTHER INFORMATION: M49 mutant

<400> SEQUENCE: 13

Gln Leu Met Lys Ser Glu Leu Glu Glu Lys Lys Phe Glu Leu Arg Arg
1               5                   10                  15

Lys Leu Lys Tyr Val Pro His Glu Tyr Ile Glu Leu Ile Glu Ile Ala
            20                  25                  30

Arg Asn Ser Thr Gln Tyr Arg Ile Phe Glu Met Lys Val Met Glu Phe
            35                  40                  45

Leu Val Lys Val Tyr Gly Tyr Arg Gly Lys His Leu Gly Gly Ser Arg
        50                  55                  60

Asn Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Ala Met Leu Arg Tyr Val Glu Glu Asn Gln Thr Arg
            100                 105                 110

Asn Lys His Ile Asn Pro Asn Glu Trp Trp Lys Val Tyr Pro Ser Ser
            115                 120                 125

Val Thr Glu Phe Lys Phe Leu Phe Val Ser Gly His Phe Lys Gly Asn
            130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
        195

<210> SEQ ID NO 14
<211> LENGTH: 196
<212> TYPE: PRT
<213> ORGANISM: Artificial Sequence
<220> FEATURE:
<223> OTHER INFORMATION: M50 mutant

<400> SEQUENCE: 14

Gln Pro Val Lys Ser Glu Leu Glu Glu Lys Lys Ala Glu Leu Arg His
1               5                   10                  15

Lys Leu Lys Tyr Val Pro His Glu Tyr Ile Glu Leu Ile Glu Ile Ala
            20                  25                  30

Arg Asn Ser Thr Gln Asp Arg Ile Leu Glu Met Met Val Met Glu Phe
            35                  40                  45

Phe Met Lys Val Tyr Gly Tyr Arg Gly Lys His Leu Gly Gly Ser Arg
        50                  55                  60

Lys Pro Asp Gly Val Ile Tyr Thr Val Gly Ser Pro Phe Asp Tyr Gly
```

```
65              70              75              80

Val Ile Val Asp Thr Lys Ala Tyr Ser Arg Gly Tyr Asn Leu Pro Ile
                85              90              95

Gly His Ala Asp Glu Met Gln Arg Tyr Val Gln Glu Asn Gln Thr Arg
            100             105             110

Asn Lys His Ile Asn Pro Asn Glu Trp Trp Lys Val Tyr Pro Ser Ser
        115             120             125

Val Thr Glu Phe Lys Phe Leu Phe Val Ser Gly His Phe Lys Gly Asn
    130             135             140

Tyr Lys Ala Gln Leu Thr Arg Leu Asn His Ile Thr Asn Cys Thr Gly
145             150             155             160

Ala Val Leu Ser Val Glu Glu Leu Leu Ile Gly Gly Glu Met Ile Arg
            165             170             175

Ala Gly Thr Leu Thr Leu Glu Glu Val Arg Ser Lys Phe Asn Asn Gly
        180             185             190

Glu Ile Asn Phe
        195

<210> SEQ ID NO 15
<211> LENGTH: 14
<212> TYPE: DNA
<213> ORGANISM: Artificial Sequence
<220> FEATURE:
<223> OTHER INFORMATION: Target Sequence of B2M_PPR(L)

<400> SEQUENCE: 15
aatggaaagt caaa                                                         14

<210> SEQ ID NO 16
<211> LENGTH: 14
<212> TYPE: DNA
<213> ORGANISM: Artificial Sequence
<220> FEATURE:
<223> OTHER INFORMATION: Target Sequence of B2M_PPR(R)

<400> SEQUENCE: 16
agcaattcag gaaa                                                         14

<210> SEQ ID NO 17
<211> LENGTH: 15
<212> TYPE: DNA
<213> ORGANISM: Artificial Sequence
<220> FEATURE:
<223> OTHER INFORMATION: Target Sequence of GFP_PPR(L)

<400> SEQUENCE: 17
acgacttctt caagt                                                        15

<210> SEQ ID NO 18
<211> LENGTH: 15
<212> TYPE: DNA
<213> ORGANISM: Artificial Sequence
<220> FEATURE:
<223> OTHER INFORMATION: Target Sequence of GFP_PPR(R)

<400> SEQUENCE: 18
cctggacgta gcctt                                                        15

<210> SEQ ID NO 19
<211> LENGTH: 96
<212> TYPE: DNA
<213> ORGANISM: Artificial Sequence
```

-continued

```
<220> FEATURE:
<223> OTHER INFORMATION: Target Site of B2M_PPR

<400> SEQUENCE: 19
tactccaaag attcaggttt actcacgtca tccagcagag aatggaaagt caaatttcct        60
gaattgctat gtgtctgggt ttcatccatc cgacat                                 96

<210> SEQ ID NO 20
<211> LENGTH: 212
<212> TYPE: DNA
<213> ORGANISM: Artificial Sequence
<220> FEATURE:
<223> OTHER INFORMATION: Target Site of GFP_PPR

<400> SEQUENCE: 20
caagttcagc gtgtccggcg agggcgaggg cgatgccacc tacggcaagc tgaccctgaa        60
gttcatctgc accaccggca agctgcccgt gccctggccc accctcgtga ccaccctgac       120
ctacggcgtg cagtgcttca gccgctaccc cgaccacatg aagcagcacg acttcttcaa       180
gtccgccatg cccgaaggct acgtccagga gc                                    212
```